United States Patent
Amador Carrascal et al.

(10) Patent No.: US 11,737,725 B2
(45) Date of Patent: Aug. 29, 2023

(54) INTELLIGENT GUIDED WAVE ELASTOGRAPHY

(71) Applicant: KONINKLIJKE PHILIPS N.V., Eindhoven (NL)

(72) Inventors: Carolina Amador Carrascal, Everett, MA (US); Francois Guy Gerard Marie Vignon, Andover, MA (US); Seungsoo Kim, Andover, MA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 118 days.

(21) Appl. No.: 17/260,583

(22) PCT Filed: Jul. 17, 2019

(86) PCT No.: PCT/EP2019/069191
§ 371 (c)(1),
(2) Date: Jan. 15, 2021

(87) PCT Pub. No.: WO2020/016269
PCT Pub. Date: Jan. 23, 2020

(65) Prior Publication Data
US 2021/0259661 A1    Aug. 26, 2021

Related U.S. Application Data

(60) Provisional application No. 62/699,789, filed on Jul. 18, 2018.

(51) Int. Cl.
*A61B 8/08* (2006.01)
*A61B 8/00* (2006.01)
(Continued)

(52) U.S. Cl.
CPC ............ *A61B 8/0858* (2013.01); *A61B 8/463* (2013.01); *A61B 8/485* (2013.01); *A61B 8/5215* (2013.01);
(Continued)

(58) Field of Classification Search
CPC ............................ A61B 8/485; G01S 7/52042
See application file for complete search history.

(56) References Cited

U.S. PATENT DOCUMENTS

2004/0133168 A1* 7/2004 Salcudean .......... A61B 17/3478
604/164.13
2007/0167777 A1* 7/2007 Abe ..................... G01S 15/8979
600/441
(Continued)

FOREIGN PATENT DOCUMENTS

CN          104398271 A    *  3/2015    ........... A61B 8/0891
JP          2000028593 A   *  1/2000

OTHER PUBLICATIONS

JP 2000028593 A (Year: 2000).*
(Continued)

*Primary Examiner* — Joel Lamprecht
*Assistant Examiner* — Nyrobi Celestine

(57) ABSTRACT

The present disclosure describes systems and methods configured to determine shear wave velocity and tissue stiffness levels of thin tissue of finite size, also referred to as bounded tissue, via shear wave elastography. Systems can include an ultrasound transducer configured to acquire echoes responsive to pulses transmitted toward a tissue. Systems can also transmit a push pulse into the tissue for generating shear waves, and tracking pulses intersecting the shear waves. The system can also apply a directional filter to received echo data and generate directionally filtered shear wave data based on a dimension and angular orientation of the bounded target relative to the ultrasound transducer. The system can (Continued)

estimate velocities of the shear waves at different shear wave frequencies based on the filtered shear wave data and angular orientation relative to the transducer, and determine a tissue stiffness value independent of the shape or form of the tissue.

16 Claims, 10 Drawing Sheets

(51) Int. Cl.
  *G01S 7/52* (2006.01)
  *G01S 15/89* (2006.01)
(52) U.S. Cl.
  CPC ............ *A61B 8/5269* (2013.01); *A61B 8/543* (2013.01); *G01S 7/52053* (2013.01); *G01S 15/8915* (2013.01)

(56) References Cited

U.S. PATENT DOCUMENTS

| | | | | |
|---|---|---|---|---|
| 2013/0131511 | A1* | 5/2013 | Peterson | G01S 7/52042 600/438 |
| 2014/0296709 | A1 | 10/2014 | Fatemi et al. | |
| 2015/0087976 | A1* | 3/2015 | Fan | G01S 7/52042 600/438 |
| 2015/0119711 | A1* | 4/2015 | Osumi | A61B 8/4416 600/443 |
| 2016/0262706 | A1 | 9/2016 | Zhao et al. | |
| 2016/0367223 | A1* | 12/2016 | Honjo | G01S 7/52042 |

OTHER PUBLICATIONS

J. Elias Jr et al., "Intraoperative application of real-time tissue elastography for the diagnosis and staging of pancreatic tumours," Pan American Health Care Exchanges (PAHCE) Conference, pp. 179-181, Mar. 2011 (Year: 2011).*
Lee et al., "Left Ventricular Wall Thickness and the Presence of Asymmetric Hypertrophy in Healthy Young Army Recruits Data From the Large Heart Study," Circulation: Cardiovascular Imaging, vol. 6, No. 2, pp. 262-267, Jan. 2013 (Year: 2013).*
CN-104398271-A (Year: 2015).*
M. W. Urban et al., "Error in Estimates of Tissue Material Properties from Shear Wave Dispersion Ultrasound Vibrometry," IEEE Transactions on Ultrasonics, Ferroelectrics, and Frequency Control, vol. 56, No. 4, p. 1-24, Apr. 2009 (Year: 2009).*
S. Chen et al, "Shearwave Dispersion Ultrasound Vibrometry (SDUV) for Measuring Tissue Elasticity and Viscosity," IEEE Transactions on Ultrasonics, Ferroelectrics, and Frequency Control, vol. 56, No. 1, p. 1-16, Jan. 2009 (Year: 2009).*
J. Gennisson et al., "Viscoelastic and Anisotropic Mechanical Properties of in Vivo Muscle Tissue Assessed by Supersonic Shear Imaging," Ultrasound in Medicine and Biology, vol. 36, No. 5, pp. 789-801, Feb. 2010 (Year: 2010).*
M. Couade et al, "Quantitative Assessment of Arterial Wall Biomechanical Properties Using Shear Wave Imaging", Ultrasound in Medicine and Biology, vol. 36, No. 10, pp. 1662-1676, Feb. 2010 (Year: 2010).*
Brum et al., "Application of 1-D Transient Elastography for the Shear Modulus Assessment of Thin-Layered Soft Tissue: Comparison With Supersonic Shear Imaging Technique," IEEE Transactions on Ultrasonics, Ferroelectrics, and Frequency Control, vol. 59, No. 4, pp. 703-714, Apr. 2012 (Year: 2012).*
PCT/EP2019/069191 ISR & WO, dated Oct. 25, 2019, 16 Page Document.
Manduca et al.: "Spatio-Temporal Directional Filtering Improved Inversion of MR Elastopgraphy Images"; Medical Image Analysis 7(4):465-73.
Arani et al.: "Cardiac Mr Elastography for Quantitative Assessment of Elevated Myocardial Stiffness in Cardiac Anyloidosis"; Journal of the American College of Cardiology, 2010, 55(13), pp. 1318-1327.
Song et al.: "Fast Shear Compounding Using Directional Filtering and Two-Dimensional Shear Wave Speed Calculation"; IEEE, 2013 Joint UFFC, EFTF and PFM Symposium, pp. 1264-1267.
Mo et al.: "Bias of Shear Wave Elasticity Measurements in Thin Layer Samples OAND a Simple Correction Strategy"; Springerplus (2016) 5:1341, pp. 1-12.
Nenadic et al. "Phase Velocities and Attenuations of Shear, Lamb, and Rayi Figh Waves in Plate-Like Tissues Submerged in a Fluid"; The Journal of the Acoustical Society of America, Dec. 2011, pp. 3549-3552.
Nenadic et al.: "Lamb Wave Dispersion Ultrasound Vibrometry (LDUV) Method for Quantifying Mechanical Properties of Viscoelastic Solids"; Phys Med Biol. 2011, 56(7), pp. 2245-2264.
Vlachopoulos et al.: "Prediction of Cardiovascular Events and All-Cause Mortality With Arterial Stiffness: A Systematic Review and Meta-Analysis"; Journal of the American College of Cardiology, 2010, vol. 55, No. 13, pp. 1318-1327.

\* cited by examiner

INTELLIGENT GUIDED WAVE ELASTOGRAPHY

CROSS-REFERENCE TO PRIOR APPLICATIONS

This application is the U.S. National Phase application under 35 U.S.C. § 371 of International Application No. PCT/EP2019/069191, filed on Jul. 17, 2019, which claims the benefit of U.S. Provisional Patent Application No. 62/699,789, filed on Jul. 18, 2018. These applications are hereby incorporated by reference herein.

TECHNICAL FIELD

The present disclosure pertains to ultrasound systems and methods for determining stiffness levels of thin tissue of finite size, also referred to as bounded tissues, using shear wave elastography.

BACKGROUND

Ultrasound shear wave elastography has been used to measure localized stiffness levels of various tissues, which may provide valuable information for detecting tissue abnormalities and diagnosing conditions such as cancer or liver fibrosis. Ultrasound shear wave elastography typically involves transmitting a "push pulse" from a transducer into a tissue, thereby generating a shear wave that propagates laterally therethrough. Tracking pulses emitted by the transducer can then be used to measure the velocity of the shear wave as it propagates, which usually fluctuates based on the stiffness of the tissue. For example, shear wave velocity in soft tissue is typically slower than shear wave velocity in hard tissue, assuming an identical push pulse is used to generate the shear wave in each tissue type. Accordingly, variation in shear wave velocity can be used to distinguish normal, soft tissues from abnormal, hard tissues.

While preexisting ultrasound elastography systems have proven effective in measuring localized tissue stiffness levels in organs like the liver, breast, prostate and thyroid, the shear wave propagation in tissues comprising such organs is mathematically modeled as shear wave propagation in thick, homogenous tissue of infinite size. As such, shear waves passing through the tissue may be largely unaffected by tissue boundaries, thereby allowing the shear waves to propagate unimpeded through the tissue. By contrast, thin tissue of finite size, bounded or semi-infinite tissues, such as cardiac and vascular tissues, tissues comprising organs such as the bladder and/or generally any tissue adjacent another tissue or material having different stiffness, restrict the spread of shear waves passing therethrough, dictating wave propagation direction and resulting complex wave fronts (generated shear wavelength being less than tissue thickness causing shear wave velocity dispersion) that typically cause underestimation of tissue stiffness. Accurate characterization of bounded tissue stiffness remains hindered by imaging modalities incapable of accounting for the complexities associated with shear wave propagation through such tissues. New ultrasound systems configured to determine the stiffness of bounded tissues via shear wave elastography are needed.

SUMMARY

The present disclosure describes systems and methods for determining shear wave propagation velocity and quantitative tissue stiffness levels within thin tissue of finite size, also referred to as bounded tissue, via shear wave elastography. Shear wave propagation velocity may be underestimated in bounded tissues due to wave mode conversion generated by wave reflections off restrictive tissue boundaries. To account for extraneous wave motion, systems herein can include a directional filter configured to filter shear wave echo data misaligned with the primary direction of shear wave propagation, which may be dictated by the tissue thickness and angular orientation relative to the ultrasound transducer. In various examples, systems herein can also be configured to determine tissue thickness and angular orientation relative to the ultrasound transducer without user input, thereby reducing the likelihood of error and biased measurements. After directional filtration, thickness and angular determinations, systems herein can estimate velocities of propagating shear waves at different shear wave frequencies based on the filtered wave data and angular orientation of the tissue relative to the ultrasound transducer. The estimated velocities can then be utilized to determine tissue stiffness in a manner that is independent of the tissue size and/or shape. A user interface included within systems herein can display one or more determinations made by the systems disclosed, along with live ultrasound images and tissue stiffness maps of the bounded target tissue. The systems and methods described herein may be utilized to determine tissue stiffness in various bounded tissues, such as vascular walls, bladder walls and/or cardiac tissues.

In accordance with principles of the present disclosure, an ultrasound imaging system for shear wave imaging can include an ultrasound transducer configured to acquire echoes responsive to ultrasound pulses transmitted toward a bounded target tissue. The system can also include a beamformer configured to transmit, from the ultrasound transducer, tracking pulses in response to a push pulse, where the push pulse generates shear waves in the bounded target tissue and the tracking pulses are spatially planned to intersect the shear waves at one or more locales. The beamformer can also be configured to receive, from the ultrasound transducer, echo signals where the tracking pulses intersected the shear waves. The system can further include a processor in communication with the beamformer which is configured to store tracking echo data generated from the received echo signals and apply a directional filter to the tracking echo data to generate directionally filtered wave data based on a dimension of the bounded target tissue and an angular orientation of the bounded target tissue relative to the ultrasound transducer. The processor can also estimate velocities of the shear waves at different shear wave frequencies based on the filtered wave data and angular orientation of the bounded target tissue relative to the ultrasound transducer, and determine a stiffness value of the bounded target tissue that is independent of a shape or form of the bounded target tissue using the estimated velocities and at least one dimensional parameter of the tissue.

In some examples, the dimension of the bounded target tissue includes a thickness of the bounded target tissue. In some embodiments, the processor can be configured to determine the thickness of the bounded target tissue by performing image segmentation of the bounded target tissue. In some examples, the processor can be configured to determine the angular orientation of the bounded target tissue relative to the ultrasound transducer. In some embodiments, the angular orientation of the bounded tissue relative to the ultrasound transducer can be determined by applying a de-speckling filter to the echo data and performing a Hough transform on the de-speckled echo data. In some examples, the angular orientation of the bounded target tissue is acute or oblique relative to the ultrasound transducer.

In some embodiments, the system can also include a user interface configured to display a B-mode image of the bounded target tissue. In some examples, the user interface can be further configured to display a movable region-of-interest box on the B-mode image. In some embodiments, the user interface can be further configured to display a live quantitative stiffness map of the bounded target tissue. In some examples, the beamformer can be further configured to control the ultrasound transducer to transmit the push pulse during a cardiac cycle phase selectable by a user. In some embodiments, the bounded target tissue includes tissue confined by one or more adjacent tissues or substances having different mechanical properties than the bounded target tissue. In some examples, the bounded target tissue includes myocardial tissue or vascular tissue.

In accordance with principles of the present disclosure, a method of shear wave imaging can involve acquiring ultrasound echoes responsive to ultrasound pulses transmitted toward a bounded target tissue; transmitting a push pulse into the bounded target tissue to generate shear waves in the bounded target tissue; transmitting tracking pulses spatially planned to intersect the shear waves at one or more locales; receiving echo signals where the tracking pulses intersected the shear waves; storing tracking echo data generated from the received echo signals; applying a directional filter to the tracking echo data to generate directionally filtered wave data based on a dimension of the bounded target tissue and an angular orientation of the bounded target tissue relative to the ultrasound transducer; estimating velocities of the shear waves at different shear wave frequencies based on the filtered wave data and angular orientation of the bounded target tissue relative to the ultrasound transducer; and determining a stiffness value of the bounded target tissue that is independent of a shape or form of the bounded target tissue using the estimated velocities and at least one dimensional parameter of the tissue.

In some examples, the dimension of the bounded target tissue includes a thickness of the bounded target tissue. In some embodiments, the angular orientation of the bounded target tissue relative to the ultrasound transducer can be determined relative to the ultrasound transducer. In some examples, the bounded target tissue can include tissue confined by one or more adjacent tissues or substances having different mechanical properties than the bounded target tissue. In some embodiments, transmitting the push pulse into the bounded target tissue can involve transmitting the push pulse during a cardiac cycle phase selectable by a user. In some examples, the method can further involve displaying an ultrasound image of the bounded target tissue and a movable region-of-interest box overlaid on the ultrasound image. In some embodiments, the thickness of the bounded target tissue can be about 1 mm to about 2 cm.

Any of the methods described herein, or steps thereof, may be embodied in non-transitory computer-readable medium comprising executable instructions, which when executed may cause a processor of a medical imaging system to perform the method or steps embodied herein.

DETAILED DESCRIPTION

Figure 1B:
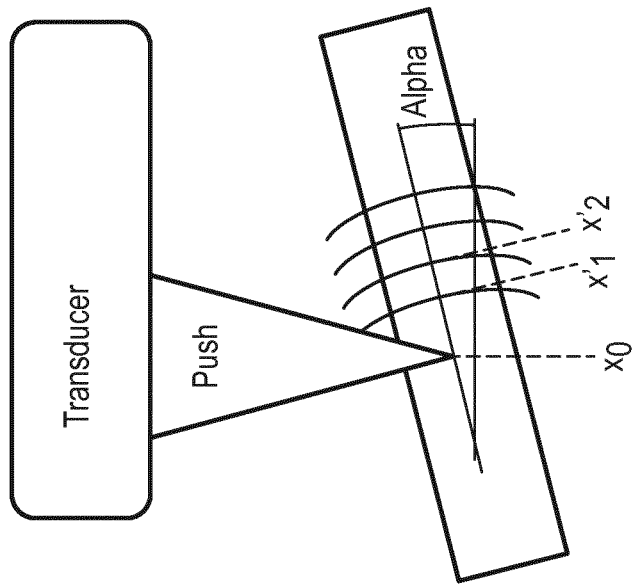
FIG. 1B is a diagram of ultrasound shear wave elastography performed in a shear wave propagation mathematical model of thin, finite, bounded, angled tissue.

The following description of certain embodiments is merely exemplary in nature and is in no way intended to limit the invention or its applications or uses. In the following detailed description of embodiments of the present systems and methods, reference is made to the accompanying drawings which form a part hereof, and which are shown by way of illustration specific embodiments in which the described systems and methods may be practiced. These embodiments are described in sufficient detail to enable those skilled in the art to practice presently disclosed systems and methods, and it is to be understood that other embodiments may be utilized and that structural and logical changes may be made without departing from the spirit and scope of the present system. Moreover, for the purpose of clarity, detailed descriptions of certain features will not be discussed when they would be apparent to those with skill in the art so as not to obscure the description of the present system. The following detailed description is therefore not to be taken in a limiting sense, and the scope of the present system is defined only by the appended claims.

The present technology is also described below with reference to block diagrams and/or flowchart illustrations of methods, apparatus (systems) and/or computer program products according to the present embodiments. It is understood that blocks of the block diagrams and/or flowchart illustrations, and combinations of blocks in the block diagrams and/or flowchart illustrations, may be implemented by computer executable instructions. These computer executable instructions may be provided to a processor, controller or controlling unit of a general purpose computer, special purpose computer, and/or other programmable data processing apparatus to produce a machine, such that the instructions, which execute via the processor of the computer and/or other programmable data processing apparatus, create means for implementing the functions/acts specified in the block diagrams and/or flowchart block or blocks.

As described herein, bounded tissue in some examples refers to tissue confined to a small cross-sectional thickness.

For example, bounded tissue may be characterized by a thickness of about 1 mm to about 2, 3, 4 or 5 mm, which may correspond to the cross-sectional thickness of vascular walls, and/or up to about 1 to about 2 cm, which may correspond to the cross-sectional thickness of various cardiac tissues. In additional examples, bounded tissue may comprise tissue adjacent to a material or tissue type having different properties, such as different tissue density. In some examples, the boundary between two adjacent materials may be abrupt or gradual. In some examples, bounded tissue may comprise tissue adjacent a liquid. For instance, bounded tissue may refer to bladder tissue adjacent to either air or urine, or vascular tissue adjacent to blood. Bounded tissue may also include tissue layered with different mechanical properties, such as various layers of skin. Generally, bounded tissue may be modeled as semi-infinite or confined tissue, through which a shear wave cannot freely propagate without contacting a boundary defined by a distinct change in tissue properties. Examples of bounded tissues contemplated herein include, but are not limited to, cardiac and vascular tissue, e.g., myocardial tissue and blood vessel walls, along with organ wall tissue, e.g., bladder wall tissue. For ease of description, the aforementioned tissue types will be referred to under the umbrella term "bounded."

Figure 1A:
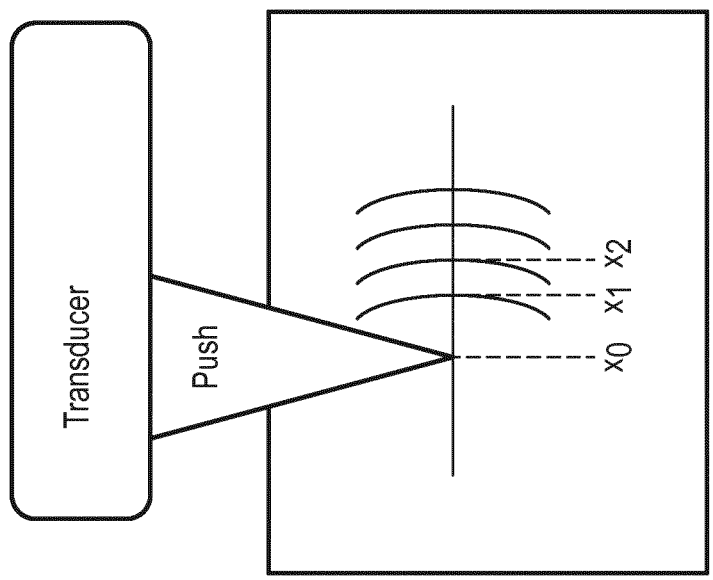
FIG. 1A is a diagram of ultrasound shear wave elastography performed in a shear wave propagation mathematical model of a thick, infinite tissue.

FIG. 1A is a diagram of ultrasound shear wave elastography performed in a model of thick, infinite tissue. Conventional shear wave elastography systems can operate under the assumption that the tissue is infinite (e.g., thickness greater than 10 cm in relatively soft material or tissue in which the shear wave wavelength is less than the tissue thickness) and unconfined for the purpose of tracking shear wave propagation. As shown, the shear wave created by transmitting a focused push pulse into the tissue spreads laterally as a planar wave, generally unaffected by rigid boundaries or abrupt changes in tissue properties. Propagation velocity of the shear wave can be accurately measured by determining the ratio of spatial resolution $(x_2-x_1)$ to wave arrival time $(t_2-t_1)$. Variation in the measured wave propagation velocity indicates variation in tissue stiffness.

FIG. 1B illustrates a generalized example of the tissue interrogated via the systems and methods described herein. As shown, the tissue is thin, finite, bounded and positioned at an oblique angle (alpha) with respect to the ultrasound transducer used to transmit push pulses. If the angle between the tissue and the transducer is not corrected, the shear wave velocity determined by the ratio of spatial resolution to wave arrival time will be biased due to the spatial resolution mismatch between the laterally separated points $(x_0, x'_1, x'_2)$ at which wave arrival time is measured. Unlike shear waves spreading unimpeded through infinite tissue, as illustrated in FIG. 1A, the shear waves propagating through semi-infinite and/or thin, finite, bounded tissues are characterized by geometric dispersion, in which wave propagation velocity varies as a function of shear wave frequency and tissue thickness. As a result, shear wave velocity may be underestimated in thinner tissues, e.g., myocardium and blood vessels, if measured using preexisting shear wave elastography systems configured to assume thick, infinite tissue geometry. Shear wave signal-to-noise (SNR) ratios may also be low, further hindering accurate shear wave detection.

Figure 1C:
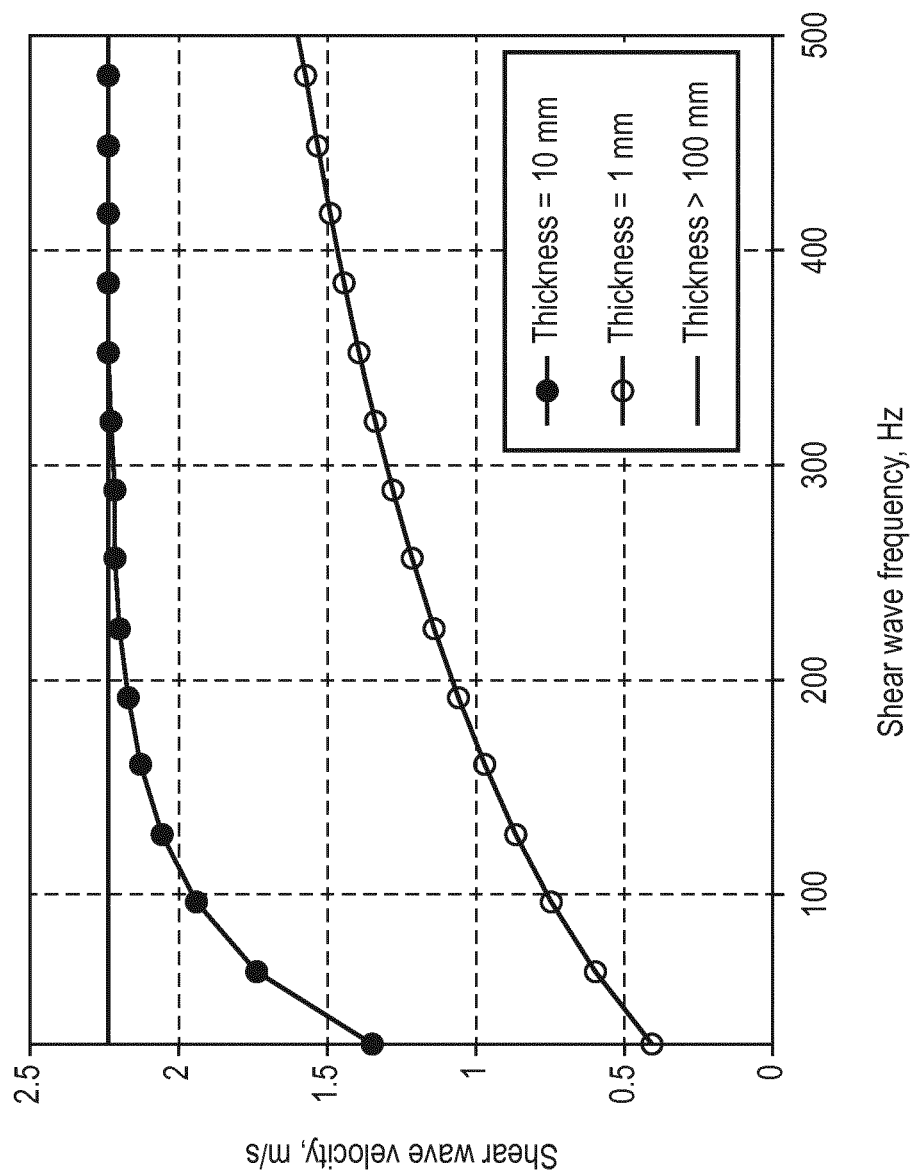
FIG. 1C is a graph showing shear wave velocity as a function of shear wave frequency measured in tissue samples varying only in thickness.

FIG. 1C is a graph of shear wave velocity as a function of shear wave frequency using a mathematical solution of the equation of motion in the case of finite tissue. This mathematical solution is known as the Lamb Wave Model. Because the tissue type is identical in all three tissue samples, the tissue stiffness is also identical; however, the difference in tissue thickness skews the shear wave velocity estimates produced using preexisting elastography approaches. Specifically, the graph shows shear wave velocity measured in a) thick, infinite tissue greater than 100 mm thick, b) thin, finite tissue of 10 mm thickness, c) and thin, finite tissue of 1 mm thickness. As shown, measured shear wave velocity remains constant regardless of shear wave frequency in the thick, infinite tissue. In the 10 mm tissue, shear wave velocity is underestimated at lower shear wave frequencies, but is more accurately estimated at higher frequencies, where the estimates conform approximately to the estimates obtained from the thick, infinite tissue. By contrast, shear wave velocity estimates are inaccurately low at all shear wave frequencies in the thinner, 1 mm tissue compared to the shear wave velocities measured in the 10 mm tissue and especially in the thick, infinite tissue. This disparity is the greatest at lower frequencies as a result of significant geometric dispersion of the shear waves. In the thick, infinite tissue, shear wave propagation is not disrupted by tissue boundaries or changes in tissue mechanical properties. In the more narrow tissues, shear wave propagation is disrupted, and the narrower the bounded tissue or the closer that neighboring tissue having different properties is to the bounded tissue, the greater the disruption. Preexisting elastography approaches are thus unable to accurately estimate tissue stiffness in a manner that is independent of tissue size, orientation and/or shape, leading to inaccurate clinical assessments. Systems provided herein are configured to accurately estimate shear wave velocity and stiffness by accounting for tissue dimensions and/or the angular orientation of the tissue with respect to the ultrasound transducer used to transmit push pulses therein.

Figure 2:
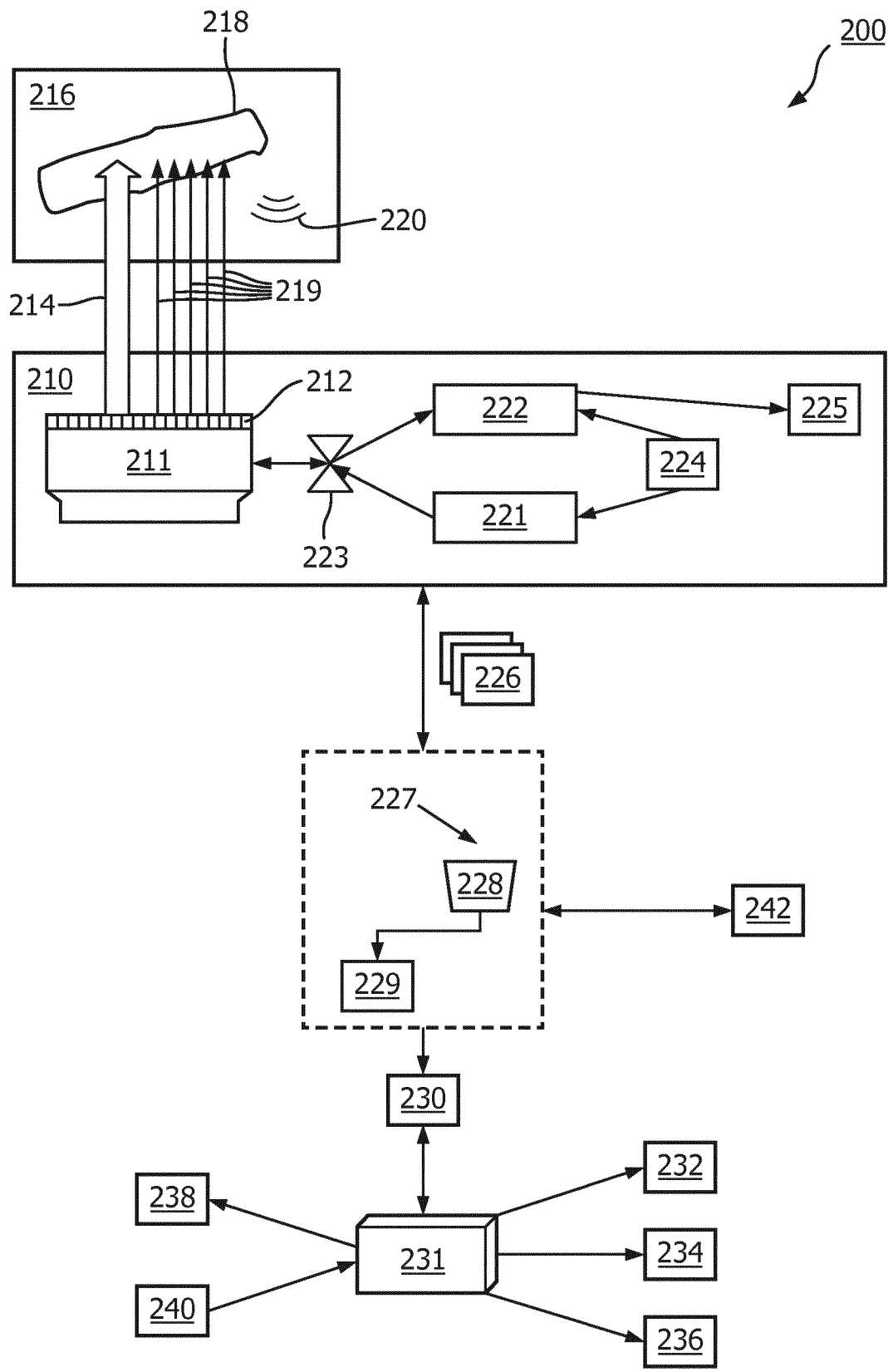
FIG. 2 is a block diagram of an ultrasonic imaging system constructed in accordance with the principles of the present invention.

FIG. 2 shows an example ultrasound system 200 configured to determine tissue stiffness characteristics in bounded tissues, which may also be angled with respect to the ultrasound transducer used to track shear waves passing through such tissues. In various embodiments, the system 200 can be configured to determine bounded tissue geometries, including tissue direction and thickness, and apply a directional filter to the shear waves passing through the tissue based on such determinations. After removing wave motion higher order modes via implementation of the directional filter, shear wave velocity can be estimated at different shear wave frequencies based on the directionally filtered data and angular orientation of the bounded tissue relative to the ultrasound transducer. A stiffness of the tissue that is independent of the shape or form of the tissue can then be estimated by the system based on the estimated velocities and at least one dimensional parameter of the tissue. In some examples, the directionally filtered shear wave velocities at several shear wave frequencies are input into the solution of the wave equation for finite tissue, a particular solution is known as the Lamb wave model, thereby producing absolute tissue stiffness determinations. As shown, the system 200 can include an ultrasound data acquisition unit 210, which can include an ultrasound probe 211 containing an ultrasound sensor array 212 configured to transmit and receive ultrasound signals. The array 212 is configured to emit an ultrasonic push pulse 214 into a target region 216 containing bounded tissue 218, e.g., an arterial wall or myocardial segment. In additional or alternative embodiments, the push pulse 214 may be generated by an array other than the array 212. For instance, in some examples, one array may be used for applying the acoustic radiation force (ARF) and a different array may be used for imaging. In yet other examples, the tissue may be stimulated mechanically, for example using an external mechanical actuator configured to apply an external mechanical force. The array 212 is also configured to transmit a plurality of tracking pulses 219 into the bounded tissue 218 to detect shear wave propagation after transmission of the push pulse. The tracking pulses 219 can be transmitted adjacent to the push pulse 214 and in some examples may be laterally-spaced with respect to the push pulse. In some embodiments, the tracking pulses 219 can be parallel to the push pulse 214, for example, when a linear probe is utilized to emit the tracking pulses. In other examples, the tracking pulses 219 may not be parallel to the push pulse 214. For instance, a curved probe may transmit tracking pulses in a radial direction with angular separation therebetween. Such pulses may not be parallel in the Cartesian space, but they are transmitted in the same direction in the polar or cylindrical coordinate frames. The array 212 is coupled to a transmit beamformer 221 and a multiline receive beamformer 222 via a transmit/receive (T/R) switch 223. Coordination of transmission and reception by the beamformers 221, 222 can be controlled by a beamformer controller 224. The multiline receive beamformer 222 can produce spatially distinct receive lines (A-lines) of echo signals, which can be processed by filtering, noise reduction, etc. by a signal processor 225. In some embodiments, the components of the data acquisition unit 210 may be configured to generate a plurality of ultrasound image frames 226 from the ultrasound echoes 220 received at the array 212. The system 200 may also include one or more processors, such as a data processor 227, which may be configured to organize A-line data into groups and detect localized movement of the bounded tissue 218 based on the data embodied in each group of A-lines. The data processor 227 can be configured to apply a directional filter 228 to the data to remove unwanted noise generated by shear waves reverberating off tissue boundaries and interfaces between the target tissue and surrounding tissues or substances. The data processor 227 can also be configured to estimate the velocity of a plurality of shear waves at different shear wave frequencies based on the filtered wave data and the angular orientation of the tissue relative to the ultrasound transducer. After estimating shear wave velocity in a manner that accounts for the angular orientation and dimensions of the target tissue relative to the ultrasound transducer, the data processor 227 can also determine the tissue's stiffness in a manner that is independent of the tissue shape, form, size or angular orientation with respect to the ultrasound transducer. In particular embodiments, the data processor 227 can input the new, filtered data into a Lamb wave model 229. As shown, the data processor 227 may include, in some examples, the directional filter 228 and the Lamb wave model 229. In some embodiments, the directional filter and/or the Lamb wave model may be implemented in one or more separate modules communicatively coupled with the data processor. Together, the components of the data acquisition unit 210 and the data processor 227 are configured to remove noise from shear waves passing through the bounded tissue 218 and accurately determine shear wave velocity and tissue stiffness independent of the angular orientation relative to the ultrasound transducer, thickness and/or shape of the tissue. Tracking displacement of the tissue may be achieved, in part, by time-interleaving the tracking pulses 219, for example as described in U.S. Application Publication No. 2013/0131511 (Peterson et al.), which is incorporated by reference in its entirety herein.

In various embodiments, the system 210 also includes a display processor 230 coupled with the data processor 227 and a user interface 231. The display processor 230 and user interface 231 can be configured to generate and display ultrasound images 232 from the image frames 226, along with tissue statistics 234, e.g., tissue thickness (in mm), cardiac cycle phase and/or shear wave velocity and/or stiffness, which may be overlaid on the images. The user interface 231 can also display a region-of-interest (ROI) box 236, which may be movable at the direction of a user, and a live tissue stiffness map 238. In some examples, the map 238 may be displayed only after application of the directional filter 228 and in some embodiments the Lamb wave model 229, while in other examples, the stiffness map can be displayed before, during and after implementation of the directional filter 228 and optionally the Lamb wave model 229, thus showing any changes in estimated stiffness values achieved via directional filtration and in some cases wave mode conversion. The user interface 231 can be configured to display the ultrasound images 232 in real time as an ultrasound scan is being performed, and may receive user input 240 at any time before, during or after a scan. The configuration of the system 200 shown in FIG. 2 may vary. For example, the system 200 can be portable or stationary. Various portable devices, e.g., laptops, tablets, smart phones, or the like, may be used to implement one or more functions of the system 200. In examples that incorporate such devices, the ultrasound sensor array 212 may be connectable via a USB interface, for example.

The system 200 can be configured to switch between multiple imaging and non-imaging modalities in response to receipt of the user input 240. One of the possible modalities includes shear wave imaging, which may contain separate sub-modalities for infinite and bounded tissue elastography, both normal and angled with respect to the push pulse transmission direction. In some examples, after the user instructs the system to enter the shear wave imaging mode for bounded tissue, a display screen configured to display a live ultrasound image may appear. In some embodiments, the user can determine the angular orientation of the bounded tissue relative to the ultrasound transducer by visually inspecting the ultrasound images, e.g., B-mode images, of the tissue. In addition or alternatively, systems herein can be configured to automatically detect the angle of the bounded tissue relative to the ultrasound transducer. The user may be presented with an option to measure tissue angle via visual inspection, aided by a digital angle measurement tool, or through automated tissue segmentation by the system.

In operation, a user of the system 200 may initially select a view of the tissue of interest. The user may then select an operational mode for performing shear wave elastography of bounded tissue, which may be indicated as the "intelligent guided wave elastography mode" in some embodiments. The user may also select a phase in the cardiac cycle, e.g., systole, diastole or trace, during which shear wave elastography is to be performed, or the system 200 may automatically select a particular phase. The region-of-interest (ROI) box 236 may then be positioned over a live ultrasound image 232 of the target bounded tissue 218 on the user interface 231, and elastography initiated by transmission of one or more push pulses and series of tracking pulses. In embodiments, a plurality of push pulses of may be transmitted into the bounded tissue 218 to generate a plurality of shear waves at a range of frequencies, enabling shear wave velocity detection at each shear wave frequency. Acquisition of image frames 226 from the tissue can initiate one or more automatic determinations of tissue parameters, e.g., tissue thickness, shape and/or angular orientation relative to the ultrasound transducer, from the echo data embodied in the image frames. In various examples, tissue segmentation may be performed, followed by the tissue angle and thickness determinations. The data processor 227 can then utilize the determined tissue thickness and angle to initialize the directional filter 228, which removes higher order motion from the echo data in the form of wave motion produced by shear wave reflections off tissue boundaries. After filtering the echo data via directional filter 228, the data processor 227 can estimate the velocities of shear waves as a function of shear wave frequency and determine the tissue stiffness in a manner that is independent of the shape or form of the bounded tissue using the estimated velocities and at least one dimensional parameter, e.g., thickness and/or angular orientation relative to the ultrasound transducer. In some specific examples, the filtered data can be fit to the Lamb wave model 229 for wave conversion and absolute tissue stiffness quantification.

As mentioned above, tissue orientation can be determined manually or automatically. Manual determination may involve measuring tissue direction through a straight line indicated on a B-mode image 232 of the tissue displayed on the user interface 231. The line can be adjusted, for example via a knob manipulated by the user. Automatic determination of tissue orientation can be performed by the data processor 227. In various embodiments, the data processor 227 can be configured to segment the tissue using ultrasound image data embodied in the image frames 226 received from the data acquisition unit 210. In specific examples, the data processor 227 can be configured to de-speckle the image by applying an unspeckling or smoothing filter to the ultrasound image pixels constituting each frame 226. After de-speckling, the data processor 227 can implement a Radon (Hough) transform of the image, or at least of the region of interest, to obtain a principle orientation of the tissue. In addition or alternatively, the data processor 227 can be configured to compute a local Haessian matrix, thereby determining the angular orientation of elongated tissue relative to the ultrasound transducer.

Tissue thickness can also be determined manually or automatically. Manual determination of tissue thickness can be achieved by direct caliper measurements of the tissue. Automatic determination of the tissue thickness can involve performing tissue segmentation techniques, which may involve heart model fitting in cardiac applications.

After the thickness and angular orientation of the bounded target tissue 218 relative to the ultrasound transducer have been determined, the directional filter 228 can be applied to remove shear wave noise, which may involve applying a narrow directivity centered about the determined tissue angle. The directivity can be adjustable in some embodiments, for example in response to a user input 240, such that the amount of noise removed can be increased or decreased. In some examples, the shear wave data can be rotated to a horizontal axis of display and the directional filter applied thereto. In other examples, an oriented directional filter can be applied. In particular embodiments, the directional filter 228 can be configured to filter the wave data by weighting the spatial frequency spectra of wave motion based on a cosine raised to the power q about the assumed direction of shear wave propagation as shown in Equation 1.1:

$$(\cos(\theta))^q = \left(\frac{k_y\cos(\alpha) - k_x\sin(\alpha)}{\sqrt{k_y^2 + k_x^2}}\right)^q \quad \text{(Equation 1.1)}$$

In Equation 1.1, $k_y$ and $k_x$ represent the directions across which spatial frequency spectra of the shear waves can be measured and filtered, a represents the rotational angle of the directional filter 228 that can be implemented via the filter's steering capability, and q controls the filter width. The unique configuration of the directional filter 228, and thus system 200, embodied in Equation 1.1, can be derived by configuring the processor to account for tissue parameters, such as thickness and angular orientation relative to the ultrasound transducer, by incorporating multiple sub-operations uniquely adapted for analyzing bounded, angled tissue. For example, Equation 1.2 embodies a 2-dimensional wave equation that preexisting directional filters may be configured to implement in infinite tissue models, in which shear waves may propagate outward from a point source, unimpeded by structural boundaries:

$$\frac{\partial^2 u}{\partial t^2} = c^2 \frac{\partial^2 u}{\partial x^2} + c^2 \frac{\partial^2 u}{\partial y^2} + f \quad \text{(Equation 1.2)}$$

where u(x,y) represents wave displacement and f is force. By implementing Equation 1.2, less sophisticated directional filters may be equipped to filter out reflecting shear waves that propagate in the backward direction, only. A more advanced directional filter can be configured to filter wave motion specifically in the $k_y$ direction according to Equation 1.3, for example as described by Manduca, A., et al. in "Spatio-temporal directional filtering for improved inversion of MR elastography images" (*Medical Image Analysis*, 2003. 7(4): p. 465-473):

$$(\cos(\theta))^q = \left(\frac{k \cdot e_y}{|k|}\right)^q = \left(\frac{k_y}{\sqrt{k_y^2 + k_x^2}}\right)^q \quad \text{(Equation 1.3)}$$

In Equation 1.3, $e_y$ represents the unit vector in the y direction. The steering capability of directional filter 228 can be added by implementing a rotational transformation to Equation 1.3 in accordance with Equations 1.4 and 1.5:

$$k'_x = k_x \cos(\alpha) + k_y \sin(\alpha) \quad \text{(Equation 1.4)}$$

$$k'_y = k_y \cos(\alpha) k_x \sin(\alpha) \quad \text{(Equation 1.5)}$$

By adding the steering capability to a directional filter limited to a single filtration axis, directional filter 228, represented in part in the example of Equation 1.1, can be obtained.

After directional filtration of the shear wave data, the data processor 227 may then be configured to perform a 2D Fourier transform analysis to estimate shear wave phase velocity at a plurality of shear wave frequencies, which can be performed by transmitting a plurality of push pulses at a variety of frequencies and/or intensity levels. In some examples, estimating shear wave phase velocity at a plurality of frequencies can be implemented by fitting the directionally filtered wave data with a Lamb wave model, thereby determining a quantitative stiffness or shear modulus estimate. According to such examples, the data processor 227 may be configured to create a look-up table of shear wave velocity corrections based on the Lamb wave model, which may be stored in a memory 242 coupled with the processor. Shear wave velocity (determined after directional filtering) and tissue thickness can be input into the table to obtain corrected shear wave velocity and/or modulus values.

The Lamb wave model 229 can be configured to perform a Lamb wave analysis of the directionally filtered shear wave data. For instance, conventional tissue stiffness estimates may be obtained by applying Equation 1.6 to shear wave data:

$$E = 3 \cdot \rho \cdot SWV^2 \quad \text{(Equation 1.6)}$$

where E is tissue stiffness, ρ is tissue density and SWV is shear wave velocity measured, for example, according to a time-to-peak approach. Lamb waves can be generated by mode conversion of shear waves in a finite medium via Lamb wave model 229. In particular, one characteristic of Lamb waves is dispersion, meaning that shear wave velocity is frequency dependent. As a result, Lamb wave dispersion and wave modes can be analyzed through k-space, which is the two-dimensional Fourier transform of the spatio-temporal shear wave motion, as described by Nenadic, I. Z., et al. in "Phase velocities and attenuations of shear, Lamb, and Rayleigh waves in plate-like tissues submerged in a fluid (L)" (*J Acoust Soc Am*, 2011. 130(6): p. 3549-52). In specific implementations, Lamb wave dispersion for bounded target tissue having plate-like geometries can be determined according to Equation 1.7:

$$4k_L^3 \beta_L \cosh(k_L h)\sinh(\beta_L h) - (k_s^2 - 2k_L^2)^2 \sinh(k_L h)\cosh(\beta_L h) = k_s^4 \cosh(k_L h)\cosh(\beta_L h) \quad \text{(Equation 1.7)}$$

where $k_L$ is the Lamb wave number, $k_s$ is the shear wave number, h is the half-thickness and β is:

$$\beta = \sqrt{k_L^2 - k_s^2} \quad \text{(Equation 1.8)}$$

By incorporating a Lamb wave analysis via Equation 1.8, estimated tissue stiffness, E, of bounded target tissues may be similar to the estimated tissue stiffness of infinite models of the same tissue type.

Figure 3A:
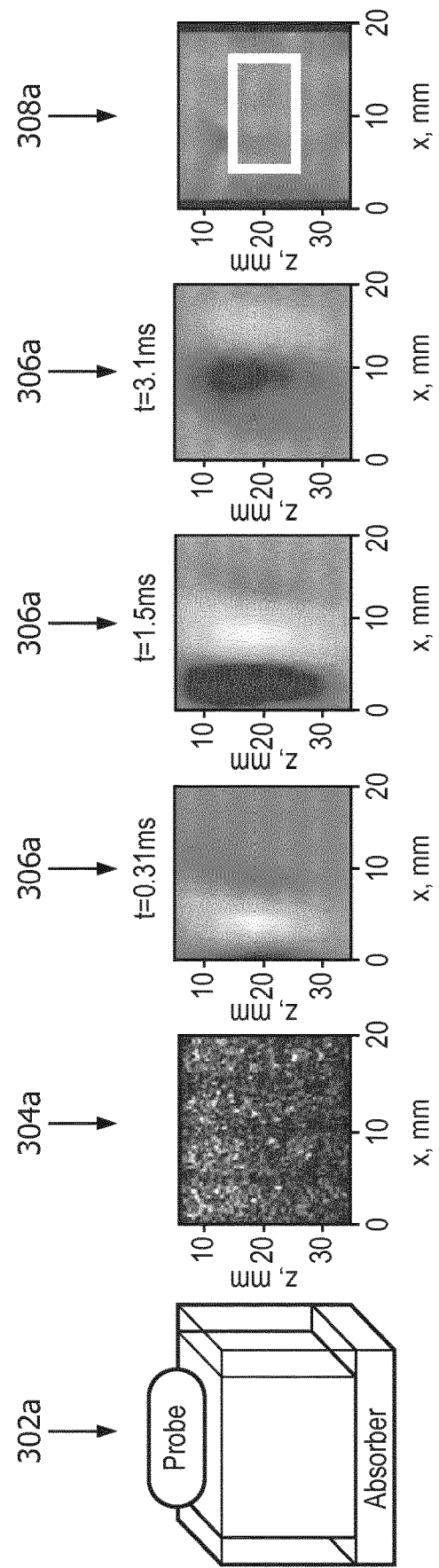
FIG. 3A provides an overview of shear wave elastography performed in a thick, infinite tissue.

FIGS. 3 and 4 illustrate various outputs generated by the data acquisition unit 210, before and after implementation of the data processor 227, directional filter 228, and in some examples, Lamb wave model 229. FIG. 3A provides an overview of shear wave elastography performed in an infinite thick phantom tissue model mimicking uniform tissue, e.g., liver tissue. The infinite model 302a assumes a thick and soft tissue, e.g., thickness >10 cm and wavelength <10 cm, sandwiched between an ultrasound probe and an absorber. The B-mode image 304a of the infinite tissue includes no immediate boundaries on any side of the tissue, allowing a shear wave to pass through the tissue without deflection. Propagation of a planar shear wave is shown in three sequential image snapshots 306a taken 0.31 ms, 1.5 ms, and 3.1 ms after push pulse transmission. Time-of-flight analysis (also referred to as time-to-peak) of the shear wave passing through the infinite tissue can be implemented to produce an accurate qualitative stiffness map 308a having a scale of 0-30 kPa. Within the ROI box overlaid on the stiffness map, tissue stiffness is substantially uniform.

Figure 3B:
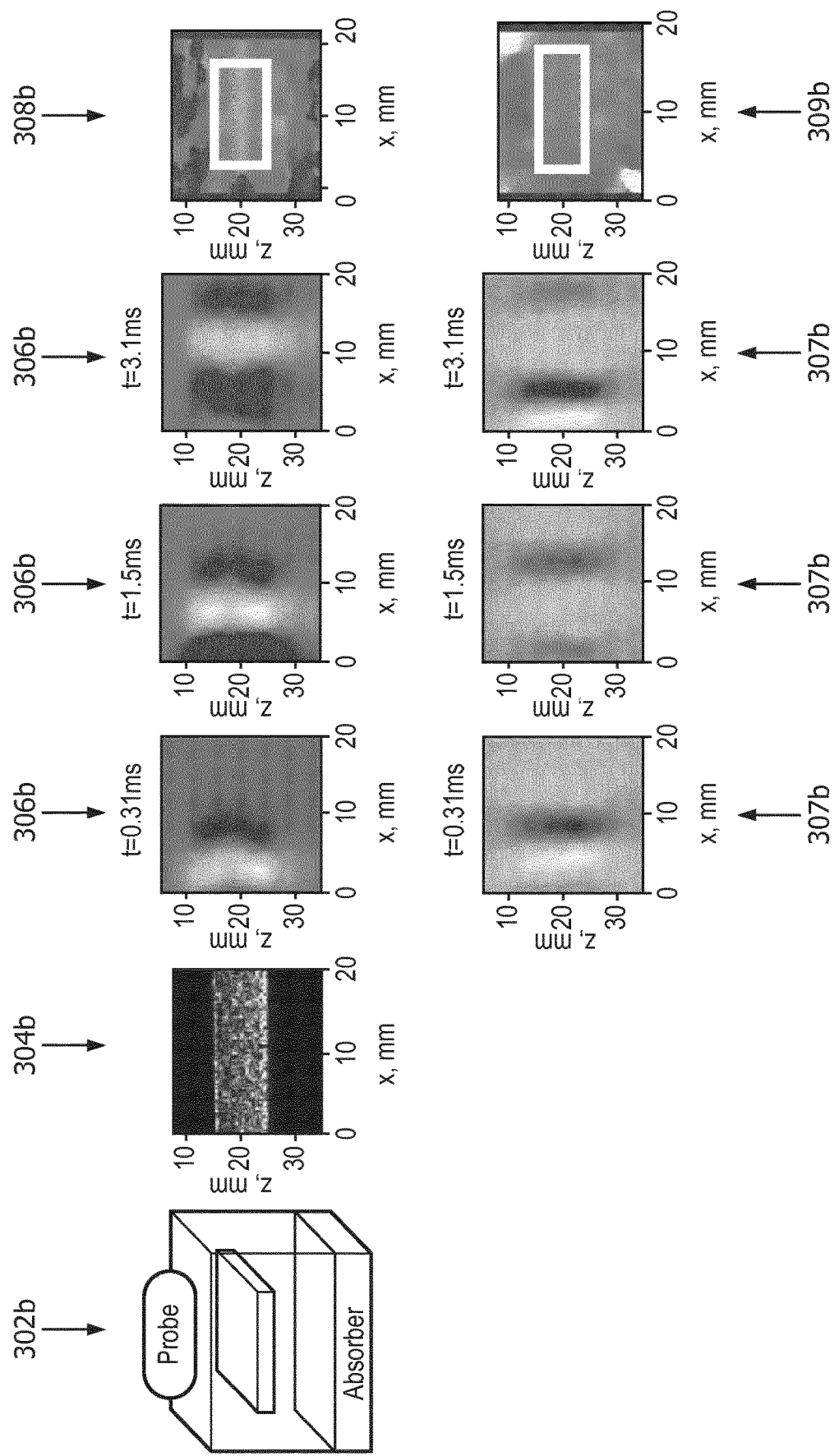
FIG. 3B provides an overview of shear wave elastography performed in a thin, finite, bounded tissue.

FIG. 3B provides an overview of shear wave elastography performed in a thin, finite, bounded tissue. The bounded tissue model 302b includes a more narrowly confined tissue compared to the infinite tissue illustrated in the infinite model 302a. In the example shown, the bounded tissue comprises a phantom tissue model having a thickness of about 1 cm. While more narrow, the tissue evaluated in the bounded tissue model 302b has the same stiffness as the infinite tissue evaluated in accordance with FIG. 3A. The B-mode image 304b of the bounded tissue shows that the tissue is confined to a cross-sectional thickness of about 10 mm. Propagation of a shear wave is shown in three sequential image snapshots 306b. Unlike the planar wave pattern generated in the infinite tissue, the shear wave reflects within the boundaries of the tissue, producing complex wave fronts. As a result, the corresponding stiffness map 308b contains localized areas of high stiffness despite the uniform stiffness of the tissue. By applying the directional filter 228 disclosed herein, such artifacts can be removed and the accuracy of the stiffness map substantially improved. This is evident in the sequential image snapshots 307b, which represent the directionally filtered versions of the snapshots 306b shown above. In this example, the directional filter 228 can be configured to filter the shear wave motion based on the primary direction of the shear wave, which in this case is the horizontal direction, perpendicular to the direction of the push pulse used to generate the shear wave. The directional filter enhances the horizontal wave motion and diminishes non-horizontal wave motion produced by shear wave reflections off the tissue boundaries. The qualitative tissue stiffness map 309b produced using the newly generated, directionally filtered data correctly shows uniform stiffness within the ROI box.

Figure 3C:
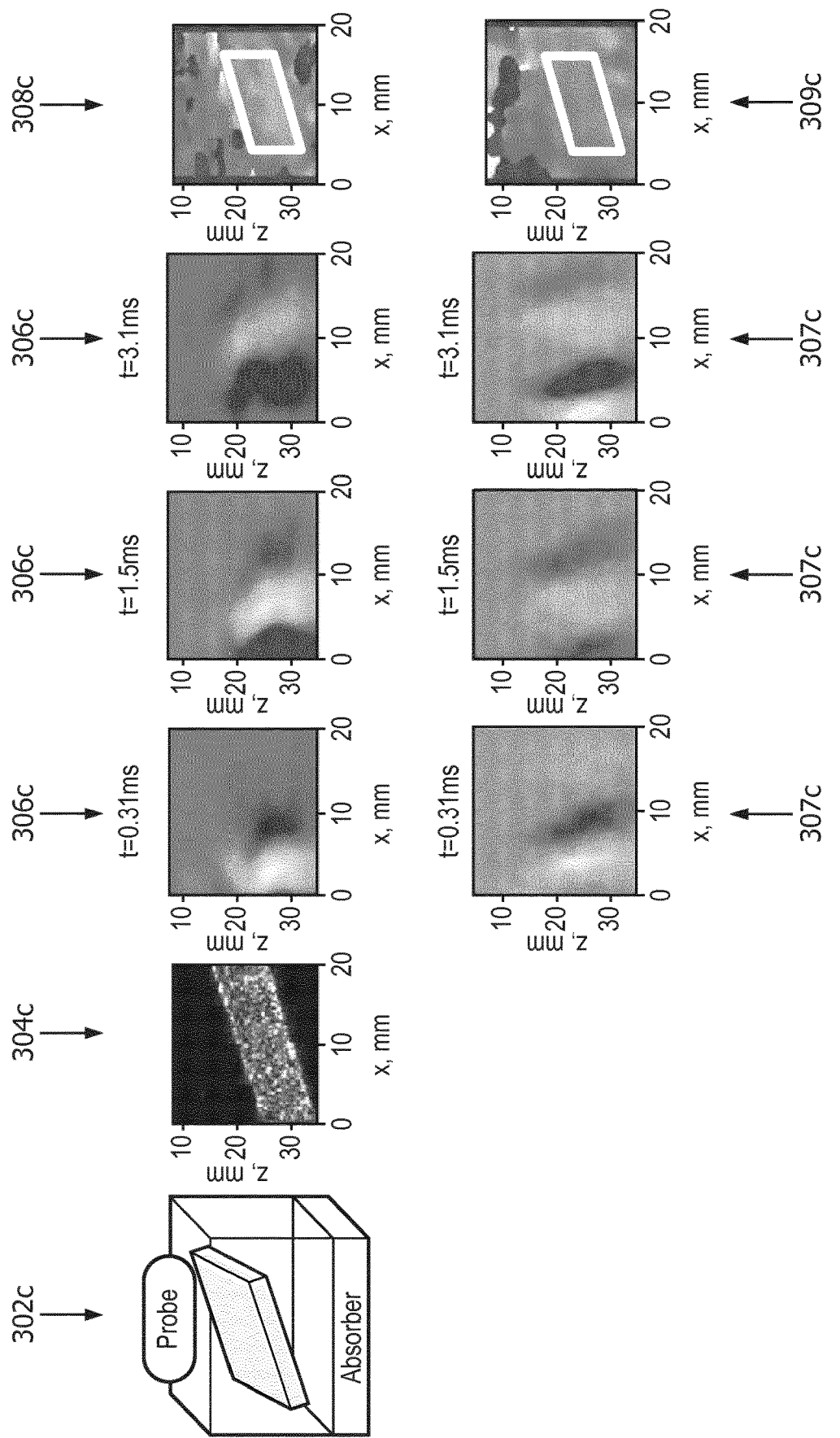
FIG. 3C provides an overview of shear wave elastography performed in a thin, finite, bounded, angled tissue.

FIG. 3C provides an overview of shear wave elastography performed in a thin finite, bounded tissue positioned at an oblique angle relative to the ultrasound probe Like the bounded tissue shown in FIG. 3B, the bounded tissue model 302c includes a bounded tissue confined to a cross-sectional thickness of about 1 cm, which is evident in the B-mode image 304c of the tissue. Propagation of an unfiltered shear wave is shown in three sequential image snapshots 306c. The shear wave reflects within the boundaries of the tissue, producing complex wave fronts, which are guided in the direction of the tissue (from lower left to upper right). As a result, the corresponding stiffness map 308c shows heterogeneous stiffness levels despite the uniform stiffness of the tissue. By applying the directional filter 228 according to the methods described herein, the image artifacts obscuring qualitative stiffness readings can be removed and the accuracy of the stiffness map substantially improved. This is shown in the sequential image snapshots 307c, which represent the directionally filtered versions of the snapshots 306c shown above. The directional filter can be configured to filter the shear wave motion based on the primary direction of the shear wave, which in this case runs from the lower left to the upper right of each image. In this manner, the directional filter 228 isolates wave motion produced from the stiffness properties of the tissue, selectively excluding wave motion caused by reflection from the tissue boundaries. The qualitative tissue stiffness map 309c produced using the directionally filtered data correctly shows uniform stiffness within the ROI box.

Figure 4A:
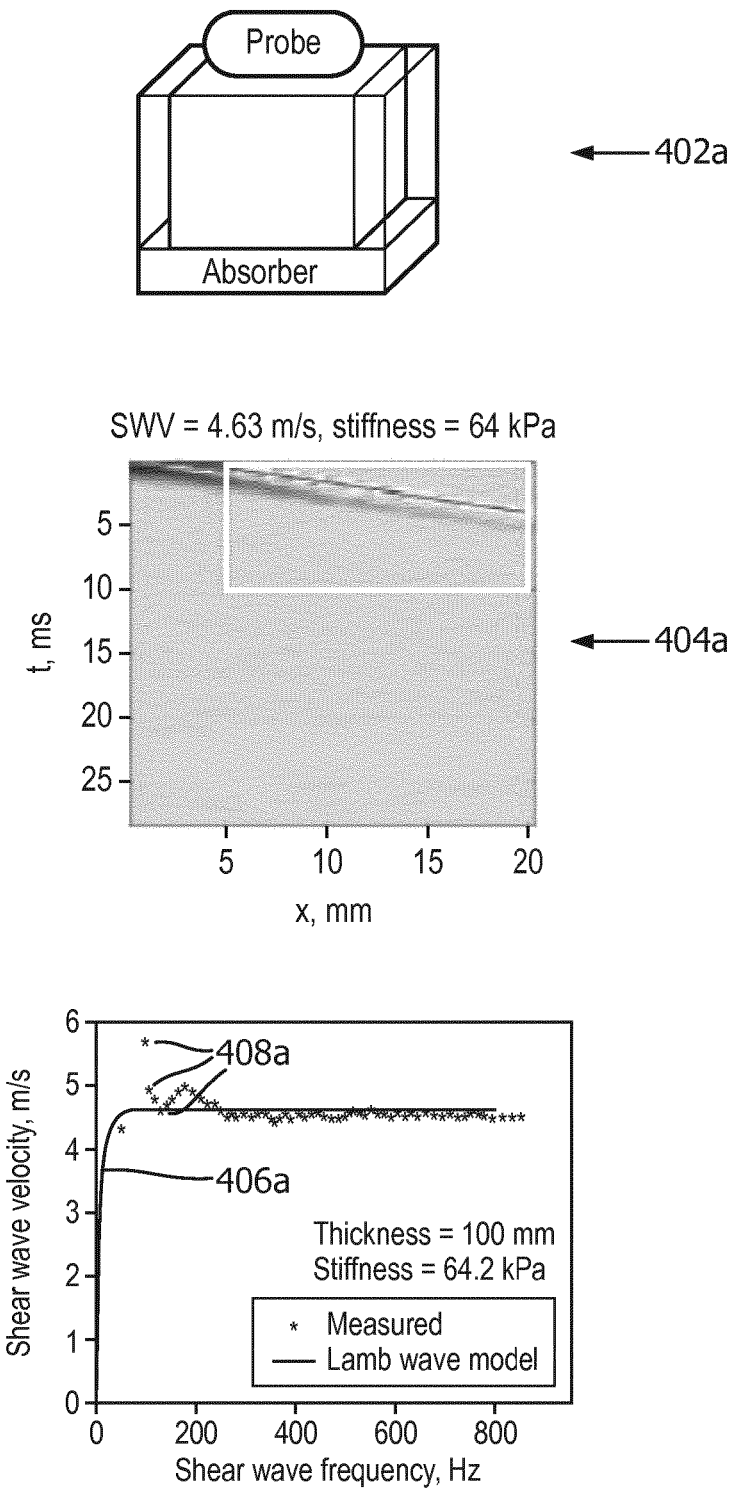
FIG. 4A provides an overview of absolute stiffness quantification of thick, infinite tissue performed in accordance with examples of the present disclosure.
Figure 4B:
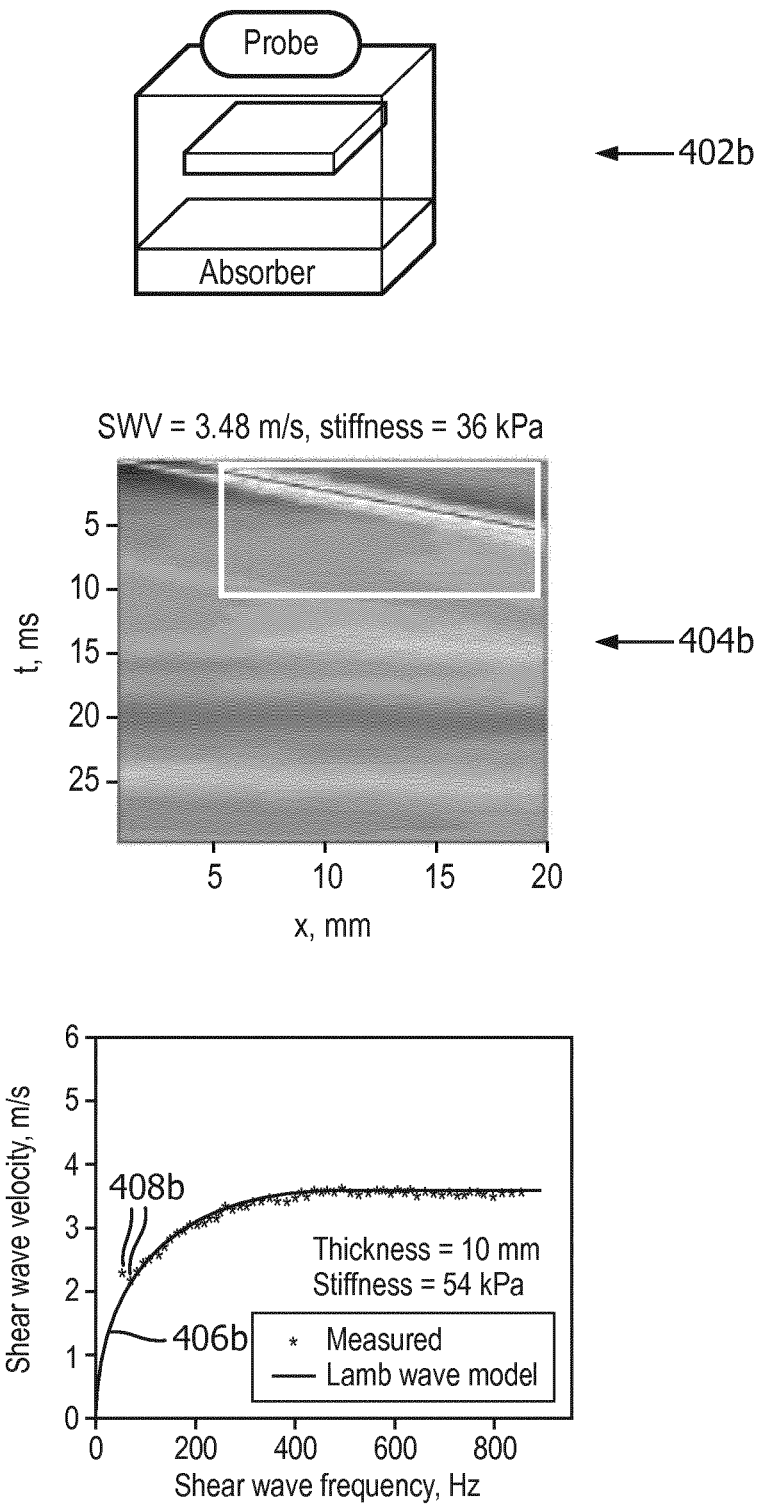
FIG. 4B provides an overview of absolute stiffness quantification of thin, finite, bounded tissue performed in accordance with examples of the present disclosure.
Figure 4C:
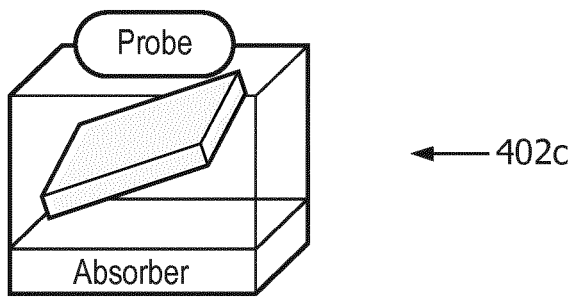
FIG. 4C provides an overview of absolute stiffness quantification of thin, finite, bounded, angled tissue performed in accordance with examples of the present disclosure.
Figure 4C:
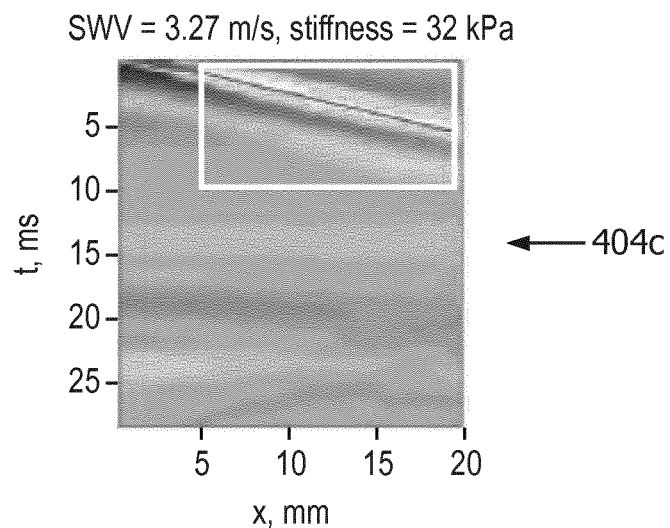
Figure 4C:
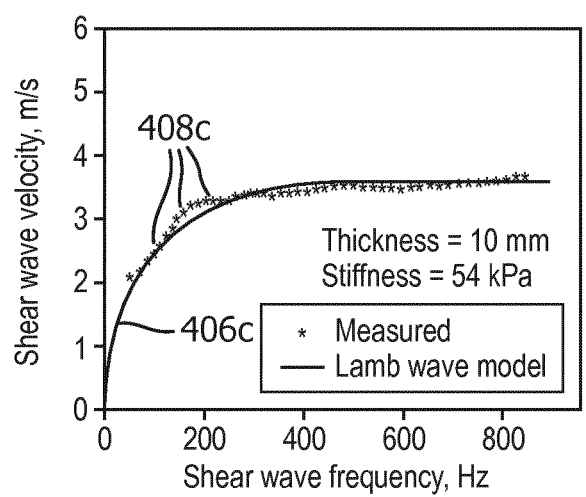

Once the boundary conditions, e.g., thickness and angular orientation, of the bounded tissue relative to the ultrasound transducer are determined, the determinations can be used to estimate the velocities of a plurality of shear waves at different shear wave frequencies, which may be performed in some examples by fitting the estimated velocities to the Lamb wave model 229. Application of the Lamb wave model 229, for example by data processor 227, yields quantitative measurements of absolute stiffness of the bounded tissue. Improvements in absolute tissue stiffness quantification yielded by the Lamb wave model are evident in FIGS. 4A-4C. FIG. 4A shows the infinite tissue model 402a and the corresponding shear wave propagation graph 404a indicating distance traveled over time. As indicated above the graph 404a, conventional time-of-flight analysis (also referred to as time-to-peak) of the shear wave yields an estimated shear wave velocity of about 4.63 m/s and a stiffness (Young's Modulus) of 64 kPa. Application of a Lamb wave model 406a to the shear wave velocity data 408a obtained at a range of shear wave frequencies yields an estimated stiffness of 64.2 kPa, which is almost identical to the stiffness estimate obtained via the stiffness equation assuming an infinite tissue geometry. By contrast, FIG. 4B shows the bounded tissue model 402b and corresponding shear wave propagation graph 404b, with an estimated shear wave velocity of only 3.48 m/s and a stiffness of 36 kPa, despite the tissue being equally stiff compared to the tissue modeled in FIG. 4A. Application of the frequency data 408b for the directionally filtered shear wave motion detected in the bounded tissue to the Lamb wave model 406b yields an estimated stiffness of 54 kPa, much closer to the stiffness estimate of the infinite tissue, thus correcting the under-estimated tissue stiffness typically produced when operating under an infinite tissue size assumption. As shown similarly in FIG. 4C, application of the Lamb wave model 406c to the frequency data 408c produced by the bounded, angled tissue model 402c changes the initial stiffness estimate of 32 kPa (404c) to a more accurate estimate of 54 kPa. The Lamb wave model provides only one example of the manner in which absolute tissue stiffness may be obtained in accordance with the embodiments described herein, which may generally involve filtering shear wave data based on a determined tissue angle and thus shear wave propagation angle, estimating shear wave velocities at different frequencies based on the angle, and using the estimated velocities and tissue geometry to determine tissue stiffness.

Figure 5:
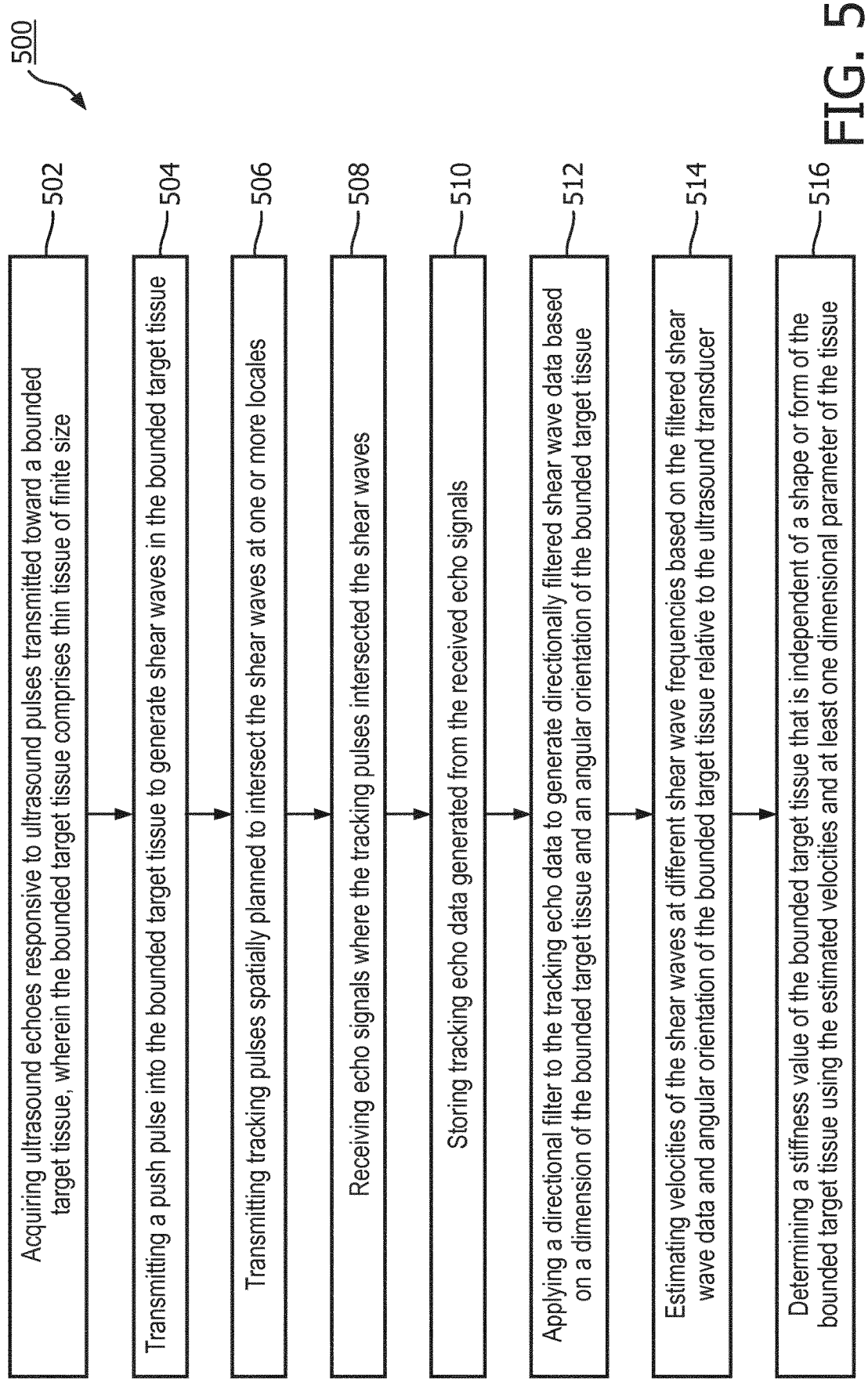
FIG. 5 is a flowchart of a method performed in accordance with principles of the present disclosure.

FIG. 5 is a flowchart of a method of shear wave imaging performed in accordance with principles of the present disclosure. The example method 500 shows the steps that may be implemented, in any sequence, by the systems and/or apparatuses described herein. The method 500 may be performed by an ultrasound imaging system, such as system 200, or other systems including, for example, a mobile system such as LUMIFY by Koninklijke Philips N.V. ("Philips"). Additional example systems may include SPARQ and/or EPIQ, also produced by Philips, which may be compatible with various cardiac probes, e.g., S5-1, linear probes, e.g., eL 18-4, and/or xMatrix probes, e.g., SWIFT XVT.

In the embodiment shown, the method 500 begins at block 502 by "acquiring ultrasound echoes responsive to ultrasound pulses transmitted toward a bounded target tissue, wherein the bounded target tissue comprises thin tissue of finite size."

At block 504, the method involves "transmitting a push pulse into the bounded target tissue to generate shear waves in the bounded target tissue."

At block 506, the method involves "transmitting tracking pulses spatially planned to intersect the shear waves at one or more locales."

At block 508, the method involves "receiving echo signals where the tracking pulses intersected the shear waves."

At block 510, the method involves "storing tracking echo data generated from the received echo signals."

At block 512, the method involves "applying a directional filter to the tracking echo data to generate directionally filtered shear wave data based on a dimension of the bounded target tissue and an angular orientation of the bounded target tissue." In some examples, prior to applying the directional filter, the method can involve determining the thickness of the bounded target tissue and/or determining an angular orientation of the bounded target tissue.

At block 514, the method involves "estimating velocities of the shear waves at different shear wave frequencies based on the filtered shear wave data and angular orientation of the bounded target tissue relative to the ultrasound transducer."

At block 516, the method involves "determining a stiffness value of the bounded target tissue that is independent of a shape or form of the bounded target tissue using the estimated velocities and at least one dimensional parameter of the tissue."

In various embodiments where components, systems and/or methods are implemented using a programmable device, such as a computer-based system or programmable logic, it should be appreciated that the above-described systems and methods can be implemented using any of various known or later developed programming languages, such as "C", "C++", "FORTRAN", "Pascal", "VHDL" and the like. Accordingly, various storage media, such as magnetic computer disks, optical disks, electronic memories and the like, can be prepared that can contain information that can direct a device, such as a computer, to implement the above-described systems and/or methods. Once an appropriate device has access to the information and programs contained on the storage media, the storage media can provide the information and programs to the device, thus enabling the device to perform functions of the systems and/or methods described herein. For example, if a computer disk containing appropriate materials, such as a source file, an object file, an executable file or the like, were provided to a computer, the computer could receive the information, appropriately configure itself and perform the functions of the various systems and methods outlined in the diagrams and flowcharts above to implement the various functions. That is, the computer could receive various portions of information from the disk relating to different elements of the above-described systems and/or methods, implement the individual systems and/or methods and coordinate the functions of the individual systems and/or methods described above.

In view of this disclosure it is noted that the various methods and devices described herein can be implemented in hardware, software and firmware. Further, the various methods and parameters are included by way of example only and not in any limiting sense. In view of this disclosure, those of ordinary skill in the art can implement the present teachings in determining their own techniques and needed equipment to affect these techniques, while remaining within the scope of the invention. The functionality of one or more of the processors described herein may be incorporated into a fewer number or a single processing unit (e.g., a CPU) and may be implemented using application specific integrated circuits (ASICs) or general purpose processing circuits which are programmed responsive to executable instruction to perform the functions described herein.

Although the present system may have been described with particular reference to an ultrasound imaging system, it is also envisioned that the present system can be extended to other medical imaging systems where one or more images are obtained in a systematic manner. Accordingly, the present system may be used to obtain and/or record image information related to, but not limited to renal, testicular, breast, ovarian, uterine, thyroid, hepatic, lung, musculoskeletal, splenic, cardiac, arterial and vascular systems, as well as other imaging applications related to ultrasound-guided interventions. Further, the present system may also include one or more programs which may be used with conventional imaging systems so that they may provide features and advantages of the present system. Certain additional advantages and features of this disclosure may be apparent to those skilled in the art upon studying the disclosure, or may be experienced by persons employing the novel system and method of the present disclosure. Another advantage of the present systems and method may be that conventional medical image systems can be easily upgraded to incorporate the features and advantages of the present systems, devices, and methods.

Of course, it is to be appreciated that any one of the examples, embodiments or processes described herein may be combined with one or more other examples, embodiments and/or processes or be separated and/or performed amongst separate devices or device portions in accordance with the present systems, devices and methods.

Finally, the above-discussion is intended to be merely illustrative of the present system and should not be construed as limiting the appended claims to any particular embodiment or group of embodiments. Thus, while the present system has been described in particular detail with reference to exemplary embodiments, it should also be appreciated that numerous modifications and alternative embodiments may be devised by those having ordinary skill in the art without departing from the broader and intended spirit and scope of the present system as set forth in the claims that follow. Accordingly, the specification and drawings are to be regarded in an illustrative manner and are not intended to limit the scope of the appended claims.

What is claimed is:

1. An ultrasound imaging system for shear wave imaging comprising:
   an ultrasound transducer configured to acquire echoes responsive to ultrasound pulses transmitted toward a bounded target tissue, wherein the bounded target tissue comprises tissue of finite size;
   a beamformer configured to:
      transmit, from the ultrasound transducer, tracking pulses in response to a push pulse, wherein the push pulse generates shear waves in the bounded target tissue and the tracking pulses are spatially planned to intersect the shear waves at one or more locales; and
      receive, from the ultrasound transducer, echo signals where the tracking pulses intersected the shear waves; and
   a processor in communication with the beamformer and configured to:
      store tracking echo data generated from the received echo signals;
      determine a thickness of the bounded target tissue and an angular orientation of the bounded target tissue relative to the ultrasound transducer and the push pulse;
      apply a directional filter to the tracking echo data to generate directionally filtered shear wave data based on the thickness of the bounded target tissue and the angular orientation of the bounded target tissue relative to the ultrasound transducer and the push pulse;
      estimate velocities of the shear waves at different shear wave frequencies based on the filtered shear wave data by fitting the filtered shear wave data to a Lamb wave model; and
      determine a stiffness value of the bounded target tissue using the estimated velocities and the thickness of the bounded target tissue and the angular orientation of the bounded target tissue.

2. The ultrasound imaging system of claim 1, wherein the processor is configured to determine the thickness of the bounded target tissue by performing image segmentation of the bounded target tissue.

3. The ultrasound imaging system of claim 1, wherein the angular orientation of the bounded target tissue relative to the ultrasound transducer is determined by applying a de-speckling filter to the echo data and performing a Hough transform on the de-speckled echo data.

4. The ultrasound imaging system of claim 3, wherein the angular orientation of the bounded target tissue is acute or oblique relative to the ultrasound transducer.

5. The ultrasound imaging system of claim 1, further comprising a user interface configured to display a B-mode image of the bounded target tissue.

6. The ultrasound imaging system of claim 5, wherein the user interface is further configured to display a movable region-of-interest box on the B-mode image.

7. The ultrasound imaging system of claim 5, wherein the user interface is further configured to display a live quantitative stiffness map of the bounded target tissue.

8. The ultrasound imaging system of claim 1, wherein the beamformer is further configured to control the ultrasound transducer to transmit the push pulse during a cardiac cycle phase selectable by a user.

9. The ultrasound imaging system of claim 1, wherein the bounded target tissue further comprises tissue confined by one or more adjacent tissues or substances having different mechanical properties than the bounded target tissue.

10. The ultrasound imaging system of claim 1, wherein the bounded target tissue comprises myocardial tissue or vascular tissue.

11. A method of shear wave imaging, the method comprising:
   acquiring ultrasound echoes responsive to ultrasound pulses transmitted toward a bounded target tissue, wherein the bounded target tissue comprises tissue of finite size;
   transmitting a push pulse into the bounded target tissue to generate shear waves in the bounded target tissue;
   transmitting tracking pulses spatially planned to intersect the shear waves at one or more locales;
   receiving echo signals where the tracking pulses intersected the shear waves;
   storing tracking echo data generated from the received echo signals;
   determining a thickness of the bounded target tissue and an angular orientation of the bounded target tissue relative to the push pulse;
   applying a directional filter to the tracking echo data to generate directionally filtered shear wave data based on the thickness of the bounded target tissue and the angular orientation of the bounded target tissue;
   estimating velocities of the shear waves at different shear wave frequencies based on the filtered shear wave data by fitting the filtered shear wave data to a Lamb wave model; and
   determining a stiffness value of the bounded target tissue using the estimated velocities and the thickness of the bounded target tissue and the angular orientation of the bounded target tissue.

12. The method of claim 11, wherein the bounded target tissue further comprises tissue confined by one or more adjacent tissues or substances having different mechanical properties than the bounded target tissue.

13. The method of claim 11, wherein transmitting the push pulse into the bounded target tissue comprises transmitting the push pulse during a cardiac cycle phase selectable by a user.

14. The method of claim 11, further comprising displaying an ultrasound image of the bounded target tissue and a movable region-of-interest box overlaid on the ultrasound image.

15. The method of claim 11, wherein the thickness of the bounded target tissue ranges from 1 mm to about 2 cm.

16. A non-transitory computer-readable medium comprising executable instructions, which when executed cause a processor of an ultrasound imaging system to perform claim 11.

* * * * *